United States Patent [19]

Yang et al.

[11] Patent Number: 4,950,689

[45] Date of Patent: Aug. 21, 1990

[54] PECTIN DELIVERY SYSTEM

[76] Inventors: Robert K. Yang, 12 Roc Etam Rd., Randolph, N.J. 07869; James J. Shaw, 34 Valley View St., Morristown, N.J. 07960; James E. Bagan, 2 Sadore La., Yonkers, N.Y. 10710; Amy J. Becker, 14 Medford Rd., Morris Plains, N.J. 07950; Shan-Shan Sheu, 20 Jean Terrace, Parsippany, N.J. 07054

[21] Appl. No.: 32,840

[22] Filed: Mar. 31, 1987

[51] Int. Cl.$^5$ .................. A23C 1/29; A61K 47/36; A61K 9/10

[52] U.S. Cl. .................. 514/777; 514/774; 514/944; 514/948; 106/209; 424/439; 424/450; 424/451; 424/452; 424/455; 424/456; 426/104; 426/573; 426/577; 426/804

[58] Field of Search .............. 514/777, 774, 944, 948; 424/439, 450, 451, 452, 456, 455; 106/209; 426/104, 573, 577, 804

[56] References Cited

U.S. PATENT DOCUMENTS

| | | | |
|---|---|---|---|
| 3,312,594 | 4/1967 | Cyr et al. | 514/774 |
| 4,576,645 | 3/1986 | Ravel et al. | 514/779 |
| 4,591,475 | 5/1986 | Tomka et al. | 424/456 |
| 4,708,834 | 11/1987 | Cohen et al. | 514/944 |
| 4,747,881 | 5/1988 | Shaw et al. | 514/778 |
| 4,753,790 | 6/1988 | Silva et al. | 424/480 |
| 4,758,598 | 7/1988 | Gregory | 514/774 |
| 4,778,676 | 10/1988 | Yang et al. | 514/774 |

*Primary Examiner*—Ronald W. Griffin
*Attorney, Agent, or Firm*—Daniel A. Scola, Jr.

[57] ABSTRACT

An ingestible gel confectionary delivery system which includes a pectin gel component in an amount sufficient to form a gel confectionary unit, and an edible insoluble solid in an amount sufficient to strengthen the internal pectin gel network and to bind internal moisture sufficiently to enhance mold removal capabilities. Preferably the delivery system also includes a further active ingredient such as a drug, medicament, or nutritional supplement. The product and method of the present invention also includes a composition in which the gel delivery system can be molded directly in the receptacle which is used to dispense the confectionary unit to the consumer. This significantly enhances the manufacture of product prepared in accordance with the invention.

34 Claims, No Drawings

PECTIN DELIVERY SYSTEM

BACKGROUND OF THE INVENTION

The present invention relates to a pectin delivery system which can be efficiently prepared and provided to the consumer as an organoleptically-acceptable confectionary product. Products prepared in accordance with the present invention provide a means whereby relatively high percentages of insoluble solids can be delivered, i.e., drugs, nutritional supplements, sweeteners and the like in a pleasing, soft gel structure.

Prescribed daily dosage amounts of fiber are often very high, requiring the patient to administer the fiber or fiber composition several times per day. While their benefits are well known to the consuming public, the unpleasant fibrous mouthfeel and texture of products containing dietary fiber has resulted in reluctance of patients to comply with prescribed dosages.

Numerous fiber-containing products are available in the market in the form of breakfast cereals, laxative beverages, bran tablets and cereal bars. Snack meals consisting of granola-type bars and cookies have become increasingly popular as a substitute for traditional meals. Although these forms of fiber are generally pleasant tasting, they typically do not deliver high concentrations of fiber and suffer from high caloric content.

The awareness of the health benefits of fiber has been largely responsible for this popularity. Yet many fiber markets have experienced a consumer reluctance to eat sufficient amounts of fiber to provide the therapeutic benefits associated with fiber. This reluctance is usually due to the objectionable taste of the fiber, or the high calories associated with masking the objectionable taste. The dry, unpalatable texture and mouthfeel of fiber often requires the incorporation of fats and carbohydrates (masking agents) in amounts which effectively dilute the fiber dosage per unit of product. Commercially available confectionary products containing fiber are generally of the granola-type. Chocolate, fruits and nuts are often added to other confectionary ingredients to enhance the palatability of the final product.

In a related disclosure, U.S. application Ser. No. 875,429, filed June 17, 1986, now U.S. Pat. No. 4,698,272, a unique confectionary form for delivering fiber is provided which includes elements of nougat technology and boiled candy technology, as well as coating technology to achieve an acceptable composition having about 20 to 30% dietary fiber present. The solution provided in the above-referenced disclosure is excellent if the consumer finds the foamed matrix described therein desirable.

Furthermore, patient compliance with prescribed drug therapies is also a problem particularly when the drug has an unpleasant taste, after-taste or gritty mouthfeel. Drugs such as phenolphthalein, dextromethorphan, danthron, sennosides, cholestyramine and potassium chloride are known to taste unpleasant. The prior art has disclosed products to mask the taste of these drugs, but the products themselves often suffer from their own unpleasant tastes or texture. The trend, therefore, in patient use of the prior art products containing fiber or drugs has been to deviate from the prescribed dosage or frequency of dosage, thereby diminishing the effectiveness of the therapy.

Two patents which disclose palatable drug formulations use coacervation techniques to combine cholestyramine with modified celluloses. U.S. Pat. No. 3,947,272 shows oral palatable formulations containing aqueous media and cholestyramine. A method of treating hypercholesterolemia is claimed. Chewable products containing cellulosic/gum colloids are disclosed.

U.K. Patent No. 1,446,352 concerns palatable compositions useful for the treatment of hypercholesterolemia and biliary cirrhosis. The invention provides a liquid composition containing "coacervate of cholestyramine with a cellulose hydrocolloid" derivative. By the term "coacervate" is meant the coagulation of two hydrophilic substances of opposite charge. Representative hydrocolloids are methyl and ethyl cellulose, sodium carboxymethyl cellulose, hydroxyethyl cellulose and hydroxypropyl cellulose. A water-insoluble dispersing agent, e.g., a substituted carboxymethyl starch, is optional. In making the composition, 1 part by weight of hydrocolloid is combined with 4 to 10 parts of cholestyramine by dry mixing and passing through a No. 80 U.S. standard mesh screen. The resulting powder is then mixed with a liquid to form a coacervate which can be orally administered.

In another related disclosure, U.S. application Ser. No. 698,511, filed Feb. 5, 1985, now U.S. Pat. No. 4,747,881, problems associated with organoleptic acceptability of fiber and drugs are remedied by formation of an aggregate having a particle size of about 4 to about 70 standard mesh. The aggregate includes a substantially anhydrous pre-swelled hydrocolloid and a substrate. Unpleasant taste and undesirable mouthfeel of fiber and/or drug is effectively masked and substantial hydration is delayed until the composition passes through the oral cavity.

While gel systems might provide an acceptable alternative delivery system, several features of gel manufacture and product characteristics discourage the use of an otherwise appealing delivery system. For example, normal gel production requires several steps generally including cooking or concentrating, depositing or moulding, drying or storing, removal from starch molds, cleaning of both the product and the mold, and sugar sanding or crystallizing or glazing. Additionally, heat sensitive active ingredients can undergo degradation since uniform distribution throughout the gel product usually requires addition of the active before cooking. Thus from a production standpoint, a gel dosage delivery system is considered much too labor-, equipment-, time-, and energy-intensive. Furthermore, it is well known that many gels resist complete dissolution in an aqueous environment and little, if any, control can be provided to the release of a unit dosage of active ingredient from the gel.

It has now been discovered, however, that the drawbacks generally occasioned by inclusion of fiber and drugs are significantly reduced and, in some cases, completely obviated by providing a gel delivery system which utilizes the natural aqueous environment of the oral cavity to mask and accelerate passage of the dissolved active ingredients during ingestion. Furthermore, the problems associated with the laborious process for preparing a suitable gel product have been overcome.

SUMMARY OF THE INVENTION

The present invention includes an ingestible gel confectionary delivery system and method of preparation thereof which includes a pectin gel component in an amount sufficient to form a gel confectionary unit and an edible insoluble solid in an amount sufficient to strengthen the internal pectin gel network and to bind internal moisture sufficiently to enhance mold removal capabilities. Preferably, the delivery system of the present invention also includes a further active component such as drug or medicament, especially a laxative. For example, the delivery system can include laxatives such as phenolphthalein, sennosides (calcium sennoside), and danthron.

The insoluble solid can be selected from one of grains, seeds, seed husks, fruits, and mixtures thereof, and it has been found to be especially effective when including dehydrated fruits in flake and powder form. Furthermore, the present invention can include the use of a humectant such as glycerin, alone or in combination with a further polymer agent such as a gelatin to enhance control of and inclusion of additional solids.

Usually, products made with the present delivery system can include pectin in an amount of from about 1 to about 5%, and preferably from about 2 to about 3% by weight, while the amount of insoluble solids can be included in an amount of from about 4 to about 20%, preferably about 4 to about 12% and most preferably from about 7.5 to about 11% of the final product. When using a laxative as an active ingredient in the present invention, the amount included can be from about 0.40% to about 2.5%, and is preferably from about 1.0% to about 2.0% by weight of the final delivery system product.

As a result of the present invention, several important advantages are obtained. First of all, the necessity of stoving to condition the gel can be reduced or practically eliminated because of the ability to initiate gelation by adjusting the insoluble solid content in addition to adjusting the pH to the proper range. Moreover, significant amounts of active ingredients such as drugs, fibers, and nutritional supplements can be incorporated without destroying the pleasant tasting chewable pectin matrix. Furthermore, stoving can be eliminated, thereby minimizing or eliminating thermal and/or hydrolytic deterioration of the active ingredient.

Furthermore, the addition of polymer network gel formers such as gelatin, or the combination of glycerin and gelatin can increase the working time prior to gelation. Increased working time provides better homogeneity to be achieved when large quantities of ingredients are to be added. This combination also supplies synergistic film-forming properties which allow the incorporation of greater quantities of insoluble solids and provides binding structure to the total gel system. Structural integrity of the gel is thus increased through the gelatin or gelatin and glycerin addition, notwithstanding the disruption of the gel's structural continuity through the addition of high amounts of insoluble solids.

Unlike other gels such as calcium alginate or xanthan-locust bean gum, pectin gels dissolve relatively quickly and completely in an aqueous environment to assure release of the active ingredient upon ingestion. Active's contained within the gel are therefore released more rapidly. Furthermore, the short texture and lubricity of the masticated particles permits the pectin based vehicle to be easily swallowed. Thus, the delivery system's texture helps to minimize the contact between the mouth taste sensors and potentially unpalatable active ingredients. This is of importance when the active ingredient being delivered is gritty as is the case with such insoluble solids as dietary fiber and cholestyramine.

Moreover, while pectin gels deliver a degree of satiety when consumed, it is also known as having desirable physiological properties such as blood sugar moderation. Furthermore the dosage form is easy to chew making it desirable for geriatric use. Additionally, the nonreversible valence pectin gel, can be detected in case there is product tampering.

For a better understanding of the present invention, together with other and further objects reference is made to the following description, and its scope will be pointed out in the appended claims.

DETAILED DESCRIPTION OF THE INVENTION

The invention involves the addition of insoluble solids directly to an ingestible pectin gel product which can be conveniently consumed as a dosage unit. The pectin gel product has, as as result of the insoluble solids, sufficient internal matrix strength to maintain individual dose units which are capable of being molded and delivered directly to the consumer in the same receptacle. This unique delivery system results from the unique composition and method.

The term "ingestible" is meant to include all materials which are used by, or which perform a function in the body. Thus, materials which are not adsorbed or absorbed are included as well as non-digestible and digestible materials.

The term "insoluble solids" as used herein means those materials which when added to the pectin gel system remain insoluble during preparation and storage, but which are released and may be solubilized during mastication and ingestion. Useful materials include seeds such as flax seeds and sesame seeds; seed husks such as psyllium; cereal brans such as oat, wheat, corn, rye, barley; legumes such as guar, pea, soybean; drugs; fruit in the form of pulp, powder, etc., and mixtures thereof.

The term "drug" includes medicaments, vitamins, mineral supplements and other chemical or biological substances intended for use in the treatment, prevention, diagnosis, cure of mitigation of disease or illness, or substances which affect the structure or function of the body.

Suitable categories of drugs that may be employed in the present delivery system may vary widely and generally represent any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chloropheniramine maleate, phenindamine tartrate, pyrilamine maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and anti-lipid agents;

(i) Antiarrhythmics such as N-acetylprocainamide;

(j) Antipyretics and analgesics such as acetaminophen, aspirin and ibuprofen;

(k) Appetite suppressants such as phenylpropanolamine hydrochloride or caffeine; and (l) Expectorants such as guaifenesin.

Additional useful active medicaments include anti-inflammatory substances, coronary dilators, cerebral dilators, peripheral vasodilators, anti-infectives, psychotropics, antimanics, stimulants, gastro-intestinal sedatives, antidiarrheal preparations, anti-anginal drugs, vasodialators, anti-hypertensive drugs, vasoconstrictors and migrane treatments, antibiotics, tranquilizers, antipsychotics, antitumor drugs, anticoagulants and antithrombotic drugs, hypnotics, sedatives, anti-emetics, anti-nauseants, anticonvulsants, neuromuscular drugs, hyper- and hypoglycaemic agents, thyroid and antithyroid preparations, diuretics, antispasmodics, uterine relaxants, nutritional additives, antiobesity drugs, anabolic drugs, erythropoietic drugs, antiasthmatics, expectorants, cough suppressants, mucolytics, anti-uricemic drugs and the like.

Mixtures of the drugs and medicaments may also be used.

The preferred drugs are laxatives, such as phenolphthlein, sennosides and danthron. Cholestyramine is also a desirable active ingredient. Cholestyramine is the chloride salt of a basic anion exchange resin which has an affinity for sodium chloride and a particularly strong affinity for acid materials such as bile acids. It occurs as an off-white powder, insoluble in water and has an amine-like odor and a gritty taste. Cholestyramine is believed to absorb and combine with bile acids in the intestine to form an insoluble complex which is then excreted by the body. Cholesterol is the major precursor of bile acids which are formed by the oxidation of cholesterol. The serum level of cholesterol can be reduced by administration of cholestyramine, which leads to reduction of bile acids and increased oxidation of cholesterol.

The recommended adult dosage of cholestyramine is about 5 to about 50 grams per day; preferably about 12 to about 32 grams per day. Administration is generally about 3 to 4 times daily in dosage of about 2 to 120 and preferably about 3 to 4 grams.

The drug component can be included in the final delivery system in pharmaceutically effective amounts up to about 20% by weight. In the case of drugs such as laxatives, the drug can be included in an amount of from about 1.0% to about 5.0%, and preferably about 2% to about 3% b weight of the final delivery system.

A suitable confectionary pectin gel delivery system in accordance with the present invention can be prepared by using the following formula:

TABLE I

| Ingredient | % by Weight |
| --- | --- |
| Pectin | 1% to about 5% |
| Water* | 40% to about 75% |
| Acidulent/Buffer | Not more than about 5% |
| Sweetener | 10% to about 60% |
| Bulking Agent | 0 to about 50% |
| Insoluble Solids | 4% to about 20%; preferably about 4 to 12% |
| Humectant | 0 to about 20% |
| Polymer Gel | 0 to about 10% |
| Flavor/Colorant | 0 to about 2% |

*It should be mentioned that the water content of the final gel, about 15 to 20%, is lower than the initial water content due to evaporation.

The gels are prepared by first combining the pectin with water to cause hydration. The pH is then adjusted to below about 4.5 by the addition of buffer, e.g., sodium citrate. Sugar and corn syrup is then added and mixed until dissolved. Up to this point, the process can be conducted at room temperature. The mixture is then boiled to obtain a desired solids content level, e.g., typically about 80 to about 90%, preferably about 81 to about 88%. The pH is again adjusted by adding a solution of acid, e.g., citric acid, to bring the pH into the gelling range of pectin.

A second mixture can then be prepared by hydrating the insoluble solids, such as dehydrated fruit, along with any other components which are to be included. These components can include humectant(s), gelatin and flavor/colorant components. The second mixture is added to the first mixture while the first mixture is still hot, e.g., at a temperature about 100° C. Mixing is a continued until uniformity is achieved. Finally, a drug component can be mixed in. The pH should be maintained throughout the procedure by use of acidulents and buffers to prevent gelation until all of the ingredients have been thoroughly blended. The pH can then be adjusted to a range of from about 3.2 to about 4.7 to provide adequate gelation. Consequently an active ingredient can be added at the end of the processing cycle thereby minimizing potential thermal deterioration of the active.

Furthermore, the addition of gelatin, or glycerin and gelation can increase the working time prior to gelation. The characteristics of a combination valence-polymer network gel permits the inclusion of added solids into the delivery system The film-forming properties of gelation thus acts synergistically with the valence gel network of pectin.

Normally, the pectin gel would have to be poured into starch molds, which requires tedious efforts to form the unit dose including cleaning both the product and the mold starch after removal of the product. In order to avoid starch moulding additional cooking is usually required to obtain the correct solids content resulting in a tough rubbery texture. However, in the present delivery system, the pectin gel will gel without stoving. Additionally, it can be poured directly into a receptacle such as a plastic blister, as opposed to convolutional starch molds, wherein the composition will gel to form a structurally coherent unit which can be dispensed intact from the blister without sticking to the plastic surface by deformation of the plastic well. Thus, the mold can serve as the final commercial container or package per se.

This result is particularly surprising in view of the nature of pectin gels. Pectin gels are valence gels which rely on hydrogen bonding to provide a coherent gel matrix. One would expect the introduction of insoluble solids into such a matrix to destroy the structural network, thereby destroying the structural integrity of the gel itself. Quite unexpectedly the present inventors have found that addition of a certain amount of insoluble solids, such as partially hydrated fruit cell wall components as well as others listed above, actually enhances the strength of the gel matrix by modifying the valence set-up sufficiently to give the product the structural integrity. Thus a unit dose can be formed and deposited directly into the final package receptacle while maintaining the desired soft, tender and chewable texture inherent to pectin.

Thus, where the soft, tender-textured pectin gel matrices have normally been used, for example, in centers of chocolate-covered jellies, etc., now a single soft-textured pectin confectionary unit having its own structural integrity can be provided. Moreover, due to the non-reversible nature of pectin gels, once set the gel will not be capable of resetting to its original form. Thus, the product is ideally suited for commercial distribution in the same mold in which it has been manufactured, since tampering would be immediately detected by evidence of product degradation or deformation.

Additionally, in those instances where a drug or nutritional supplement would be adversely affected by Schiff base type interaction with reducing sugars, a sugarless system can be employed. In this case hydrogenated starch hydrolysate could be used to replace sucrose and doctoring syrup. Depending on the carbohydrate profile selected, a texture resembling a sucrose gel can be obtained at varying added solids levels.

The sweeteners used in the present delivery system can be natural sweeteners including but not limited to sucrose, fructose, xylose, ribose, glucose, mannose, galactose, corn syrup, hydrogenated starch hydrolysate, sugar alcohols and mixtures thereof. Artificial sweeteners can also be used, such as saccharin salts, cyclamate salts, acesulfame salts, dipeptide based sweeteners, talin, monellin, dihydrochalcone and mixtures thereof.

The use of sugarless polyols in the present system permits a texture comparable to sucrose gels made with considerably lower solids, thereby permitting inclusion of a greater amount of active ingredient in the product without adversely affecting the final texture.

An especially effective formulation for the present delivery system is set forth below.

TABLE II

| Ingredient | % by Weight |
| --- | --- |
| Pectin | 2% to about 3% |
| Water | 15% to about 20% |
| Acidulent/Buffer | 1.2% to about 3.5% |
| Sugar | 36% to about 50% |
| Corn Syrup Solids | 5% to about 12% |
| Dehydrated Fruit | 7.5% to about 11% |
| Glycerin | 0% to about 20% |
| Gelatin | 0% to about 10% |
| Flavor/Colorant | 0% to about 2% |

Upon chewing, the short-texture and lubricity of the masticated particles permit the pectin delivery system to be easily swallowed. The system's texture helps to minimize the contact between the mouth taste sensor and potentially unpalatable active ingredients, and, unlike certain other gels such as calcium alginate or xantham-locust bean gum, pectin gels dissolve completely in an aqueous environment to assure release of the active ingredient. Thus, the unit dosage form is easy to chew, making it desirable for geriatric use. Moreover, pectin gels deliver a degree of satiety when consumed, and pectin has acknowledged desirable physiological properties such as blood sugar and moderation.

EXAMPLE 1

About 4.375 grams of citric acid and 4.46 grams of sodium citrate were dissolved in 250 grams of water. To this was added 11.815 grams standard 150 grade slow-set pectin, 315 grams sucrose and 36.75 grams corn syrup solids (24 D.G.). This mixture was boiled to achieve about 88% solids.

To this first mixture was added a paste containing 36.75 grams dehydrated apples, 15.75 grams dehydrated cranberries, 8.86 grams white phenolphthalein and 52.5 grams of water. These mixtures were blended until the two became uniformly dispersed in each other.

About 3.5 grams citric acid dissolved in 5.25 grams of water was added and mixed until a uniform mixture was achieved. The gel formulation was deposited into 3.5 gram pieces each one of which contained about 0.065 grams of phenolphthalein.

The resulting product appeared as firm attractive unit doses which were easy to chew and did not manifest the unpleasant, bitter flavor normally associated with this active ingredient.

EXAMPLE 2

About 8.66 grams of citric acid and 9.82 grams of sodium citrate were dissolved in 475 grams of water. To this was added 28.63 grams standard 150 grade slow-set pectin and 627 grams sucrose. This mixture was boiled to achieve about 83% solids.

To this first mixture was added 20 grams of 250 bloom gelatin hydrated with 100 grams of water, blended in a paste containing 30.0 grams dehydrated apples, 35.0 grams dehydrated cranberries, 25.0 grams of glycerin, 1.275 grams flavor and 4.33 grams of citric acid and 5.94 grams of water. These mixtures are blended until the two are uniformly dispersed in each other.

To 200 grams of this base was added 22.2 grams refined corn bran, and to another 200 grams batch was added 7.16 grams of a granulated corn bran mixture comprised of 3 parts of corn bran to one part of guar gum to one part of pulverized sugar.

The resulting composition was poured into blister wells provided in a plastic sheet. A self-sustaining gel product was formed in each of the blister wells. This product was easily dispensed by deforming the respective well, and there was no residual gel remaining in the well.

EXAMPLE 3

About 8.66 grams of citric acid and 9.82 grams of sodium citrate were dissolved in 475 grams of water. To this was added 28.63 grams standard 150 grade slow-set pectin and 637 grams sucrose. The mixture was boiled to achieve about 83% solids.

To this first mixture was added 20 grams of 250 bloom gelatin hydrated with 100 grams of water, blended in a paste containing 265.0 grams psyillium seed husk and 73.6 grams of glycerin. 4.33 grams of citric acid dissolved in 5.94 grams of water was added and after mixing until uniform, the resulting product was spread as a slab and allowed to solidify.

The product was a continuous gel matrix which did not exhibit stickiness and which presented a pleasing texture to the consumer.

EXAMPLE 4

About 87.5 grams of citric acid and 8.92 grams of sodium citrate were dissolved in 450 grams of water. Then 23.63 grams of standard 150 grade pectin dry blended with 130 grams of sugar were added while stirring. This mixture was boiled for about 1 minute, after which a dry blend of 500 grams of sugar and 105 grams of corn syrup solids was added. Boiling continued until the mixture attained about 87% solids.

Immediately upon reaching 87% solids, 7 grams of citric acid in 10.5 grams of water was added along with a paste composed of 6.46 grams of apple flakes, 2.77 grams of cranberry powder, and 1.56 grams of white phenolphthalein in water. Finally, a citric acid solution containing 7 grams of citric acid was added and the composition was deposited into truncated cone blisters of coextruded polypropylene/ ethylene vinyl alcohol/-polypropylene blisters with paper/ foil/heat seal coated lidding.

The product provided commercial unit doses which were pleasing to the consumer and which were easily removed from the blister packaging.

EXAMPLE 5

In another run, 7.875 grams of citric acid and sodium citrate were dissolved in 420 grams of water to which a preblend 23.628 grams of 150 standard grade slow-set pectin and 100 grams of sugar was mixed until lump free. Then 105.00 grams of corn syrup solids and 530 grams of sugar were added and boiled until reaching 88.1% solids content.

Another 7.875 grams of citric acid dissolved in 10.5 grams of water was blended until uniformly dispersed. A paste was formed containing 73.5 grams apple flakes, 31.5 grams cranberry powder, 0.34 grams red coloring agent (FD&C Red #40), and 19.58 grams of danthron (1,8-dihydroxyanthraquinone) in 105 grams of water. The paste was blended into the gel base until uniform, then it was deposited into blister molds and packaged in foil film seal pouches The product was an excellently-textured gel product which was easily removed from the blister without appreciable residual gel sticking to the blister.

EXAMPLE 6

In a large batch production run, 315 grams of citric acid and 357 grams of sodium citrate were dissolved in 1000 grams of water, and a separate solution of 315 grams of citric acid in 420 grams of water was prepared. A dry mix of 945 grams of 150 standard grade slow-set pectin and 2800 grams of fine granulated sugar was blended with a second dry mix of 9 lbs. 4 oz. of corn syrup solids and 49 lbs. 5 oz. of sugar. The resulting blend was added to 34 lbs. 3 oz. water and the citric acid/sodium citrate solution added thereto.

The batch was boiled to an 88.1% solids content after which the separate citric acid solution was added along with a paste which included 6.5 lbs. apple flakes, 2.778 lbs. cranberry powder, and 135 grams of calcium sennoside (an anthraquinone glucoside) in about 9.25 lbs of water. The overall mixture was transferred to a deposit hopper and maintained a temperature of about 200°-210° F. while depositing into polypropylene blister trays at about 4.25 grams per piece. The trays were then heat sealed with aluminum laminate lidding.

As in the bench scale runs, the product resulting from the large batch preparation was a very pleasing confectionary unit which was easily dispensed by deformation of the blister.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:
1. An ingestible gel confectionary delivery system comprising
    a pectin gel component in an amount sufficient to form a gel confectionary unit, and
    an edible insoluble solid in an amount sufficient to strengthen the internal gel network such that the gel retains its structural integrity during mold removal.

2. The delivery system of claim 1 which further comprises a nutritional supplemental and/or a drug or medicament selected from the group consisting of analgesics, antipyretics, antiarrhythmics, ion exchange resins, vitamins, anti-inflammatory substances, coronary dilators, cerebral dilators, peripheral vasodilators, anti-infectives, psychotropics, antimanics, stimulants, antihistamines, laxatives, decongestants, gastro-intestinal sedatives, antidiarrheal preparations, anti-anginal drugs, vasodilators, anti-hypertensive drugs, vasoconstrictors and migraine prophylaxis drugs, antibiotics, tranquilizers, antipsychotics, antitumor drugs, anticoagulants and antithrombotic drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucolytics, anti-uricemic drugs and mixtures thereof.

3. The delivery system of claim 2 wherein said drug is a laxative.

4. The delivery system of claim 3 wherein said laxative is selected from the group consisting of phenolphthalein, sennosides and danthron.

5. The delivery system of claim 1 wherein said insoluble solid is selected from the group consisting of grains, seeds, seed husks, fruits and mixtures thereof.

6. The delivery system of claim 5 wherein said grains include cereal brans selected from the group consisting of corn, wheat, oats, rye, barley bran, and mixtures thereof.

7. The delivery system of claim 5 wherein said fruits are dehydrated apples and cranberries.

8. The delivery system of claim 5 wherein said seed husk is psyillium seed husk.

9. The delivery system of claim 1 which further comprises other polymer network gel forming agents.

10. The delivery system of claim 9 wherein said gel forming agent is gelatin included in an amount of from about 0 to about 10%.

11. The delivery system of claim 1 which further incorporates a humectant.

12. The delivery system of claim 11 wherein said humectant is glycerin added in an amount of from about 0 to about 20%.

13. The delivery system of claim 1 wherein said pectin is included in an amount of from about 1% to about 5% by weight of the final delivery system.

14. The delivery system of claim 13 wherein said amount is from about 2 to, about 3%.

15. The delivery system of claim 1 wherein said edible insoluble solid is included in an amount of from about 4 to about 20% by weight of the final system.

16. The delivery system of claim 15 wherein said amount is from about 7.5 to about 11%.

17. The delivery system of claim 1 which further comprises a sweetener, a drug ingredient, a bulking agent, acidulent/buffer ingredient, water, humectants, gel forming agents and flavor.

18. The delivery system of claim 17 wherein said delivering system has the following final general formula:

| Ingredient | % by Weight |
| --- | --- |
| Pectin | 1% to about 5% |

-continued

| Ingredient | % by Weight |
|---|---|
| Water | 15% to about 20% |
| Acidulent/Buffer | Not more than about 5% |
| Sweetener | 10% to about 60% |
| Bulking Agent | Not more than about 50% |
| Insoluble Solids | 4% to about 12% |
| Humectant | Not more than about 20% |
| Gelatin | Not more than about 10% |
| Flavor/Colorant | Not more than about 2% |

19. The delivery system of claim 18 wherein said formula is as follows:

| Ingredient | % by Weight |
|---|---|
| Pectin | 2% to about 3% |
| Water | 15% to about 20% |
| Acidulent/Buffer | 1.2% to about 3.5% |
| Sugar | 36% to about 50% |
| Corn Syrup Solids | 5% to about 12% |
| Dehydrated Fruit | 7.5% to about 11% |
| Glycerin | 0 to about 20% |
| Gelatin | 0 to about 10% |
| Flavor/Colorant | 0 to about 2% |

20. The delivery system of claim 18 which further comprises a drug in a unit dosage amount.

21. The delivery system of claim 20 wherein said drug is a laxative included in an amount of from about 0.40% to about 2.5% by weight of the final delivery system product.

22. The delivery system of claim 21 wherein said amount is from about 1.0% to about 2.0%.

23. The delivery system of claim 18 wherein said sweetener is selected from the group consisting of fructose, sucrose, xylose, ribose, galactose, mannose, glucose, corn syrup, hydrogenated starch hydrolysate, sugar alcohols and mixtures thereof.

24. The delivery system of claim 23 wherein there is additionally added a sweetener selected from the group consisting of saccharin salts, cyclamate salts, acesulfane salts, dipeptide based sweeteners, talin, monellin, dihydrochalcone and mixtures thereof.

25. A method of providing an ingestible gel delivery system formed during processing as a confectionary unit in a mold receptacle and capable of being dispensed directly from said receptacle by a consumer, comprising the steps of:
(A) providing the following ingredients:
 (a) a pectin gel component in an amount sufficient to form a gel confectionery unit, and
 (b) an edible insoluble solid in an amount sufficient to strengthen the internal gel network such that the gel retains its structural integrity during mold removal,
(B) admixing the pectin gel component with water to form a pectin gel composition,
(C) admixing the edible insoluble solid with the pectin gel composition to form a homogeneous composition,
(D) depositing said homogeneous composition into said mold receptacle, and
(E) allowing said composition to gel to said ingestible gel delivery system.

26. The method of claim 25 wherein said molds are plastic or aluminum blister receptacles.

27. The method of claim 26 wherein the amount of pectin is from about 1% to about 5% by weight of the final delivery system.

28. The method of claim 27 wherein said amount is from about 2% to about 3%.

29. The method of claim 25 wherein said solids are added in an amount of from about 4% to about 20% by weight of the final delivery system.

30. The method of claim 29 wherein said amount is from about 7.5% to about 11%.

31. The method of claim 25 wherein time of gelation is controlled by use of buffer/acidulent and insoluble solids components.

32. The method of claim 25 wherein the amount of solids added is increased by use of polymer network gels and humectants.

33. The method of claim 32 wherein said gel is gelatin and said humectant is glycerin.

34. A confectionary dosage unit comprising a pectin gel delivery system having a pectin gel component in an amount sufficient to form a gel confectionary unit and an edible insoluble solid in an amount sufficient to strengthen the internal gel network such that the gel retains its structural integrity.

* * * * *